(12) United States Patent
Ding et al.

(10) Patent No.: US 6,998,507 B1
(45) Date of Patent: Feb. 14, 2006

(54) HYDROGENATION OF METHYLENEDIANILINE

(75) Inventors: Hao Ding, Macungie, PA (US); Anthony Rocco Cartolano, Orefield, PA (US); Vipul P. Dholakia, Macungie, PA (US); Gamini Ananda Vedage, Bethlehem, PA (US)

(73) Assignee: Air Products and Chemicals, Inc., Allentown, PA (US)

( * ) Notice: Subject to any disclaimer, the term of this patent is extended or adjusted under 35 U.S.C. 154(b) by 0 days.

(21) Appl. No.: 10/925,105

(22) Filed: Aug. 24, 2004

(51) Int. Cl.
*C07C 209/77* (2006.01)

(52) U.S. Cl. .................................................. 564/451
(58) Field of Classification Search ................ 564/451
See application file for complete search history.

(56) References Cited

U.S. PATENT DOCUMENTS

| | | | |
|---|---|---|---|
| 2,511,028 A | | 6/1950 | Whitman |
| 2,606,924 A | | 8/1952 | Whitman |
| 2,606,925 A | | 8/1952 | Whitman |
| 2,606,928 A | | 8/1952 | Barkdoll et al. |
| 3,591,635 A | | 7/1971 | Farrissey, Jr. et al. |
| 3,636,108 A | | 1/1972 | Brake |
| 3,644,522 A | | 2/1972 | Brake et al. |
| 3,697,449 A | | 10/1972 | Brake |
| 3,856,862 A | | 12/1974 | Chung et al. |
| 3,959,374 A | | 5/1976 | Brennan et al. |
| 4,448,995 A | | 5/1984 | Allen |
| 4,754,070 A | | 6/1988 | Casey et al. |
| 5,196,587 A | | 3/1993 | Vedage et al. |
| 6,077,975 A | * | 6/2000 | Langer et al. ............... 564/450 |
| 6,184,416 B1 | | 2/2001 | Ding et al. |
| 6,506,361 B1 | | 1/2003 | Machado et al. |

FOREIGN PATENT DOCUMENTS

WO   WO 02/30851 A2   4/2002

OTHER PUBLICATIONS

A. Parmaliana, et al., "Catalytic Activity of Honeycomb Catalysts. I. The Benzene-Cyclohexane (de)Hydrogenation Reaction," React. Kinet. Catal. Lett., 18(3-4), pp. 295-299 (1981).
A. Parmaliana, et al., "Benzene Hydrogenation on Nickel/Honeycomb Catalysts," React. Kinet. Catal. Lett., 19(1-2), pp. 155-160 (1982).
A. Parmaliana, et al., "A Kinetic Study of the Hydrogenation of Benzene Over Monolithic-Supported Platinum Catalyst," Appl. Catal., 7(2), pp. 221-232 (1983).
A. Parmaliana, et al., "A Kinetic Study of Low Temperature Hydrogenation of Benzene Over Monolithic-Supported Platinum Catalyst," Appl. Catal., 12(1), pp. 49-57 (1984).

* cited by examiner

*Primary Examiner*—Brian Davis
(74) *Attorney, Agent, or Firm*—Michael Leach

(57) ABSTRACT

The invention is directed to an improvement in a catalytic process for the ring hydrogenation of a methylenedianiline feedstock, including crude methylenedianiline. One component of the improvement is a pretreatment process which resides in passing the crude methylenedianiline feedstock over a ruthenium catalyst carried on a fixed bed support, cooling without venting, and then hydrogenation of the pretreated crude methylenedianiline feedstock over a rhodium catalyst or a mixed Rh/Ru catalyst carried on a monolith support and carrying out the ring hydrogenation in a batch reaction. Another component in the improvement is the employment of a catalyst comprised of rhodium and ruthenium carried on a monolith support.

19 Claims, 1 Drawing Sheet

HYDROGENATION OF METHYLENEDIANILINE

BACKGROUND OF THE INVENTION

Commercial scale hydrogenation of functionalized aromatics, such as methylenedianiline, is typically carried out using slurry catalysts. The resulting methylene di(4-aminocyclohexane) has to be separated by filtration from the slurry catalyst after the completion of the hydrogenation. The product/catalyst separation step adds significantly to the production cycle time and to the cost of manufacture due to the high cost of recycling precious metal catalysts.

Slurry catalysts present problems in industrial processes due to the inherent recovery problems. These catalysts are recovered from the reaction product by filtration means. Such filters often become plugged. In addition, some of the catalyst is lost in the filtration step.

The following patents are provided to illustrate various process for the ring hydrogenation of methylenedianiline using slurry catalysts:

U.S. Pat. Nos. 2,511,028; 2,606,924; 2,606,925; and 2,606,928 disclose a general process to hydrogenate methylenedianiline(MDA) to bis(para-aminocyclohexyl)methane (PACM) using a supported ruthenium catalyst under pressures in excess of 200 psig (1480 kPa), preferably in excess of 1,000 psig (6996 kPa), at temperatures within a range of 800 to 275° C. The hydrogenation is carried out under slurry conditions with an inert organic solvent. Under these conditions, the reaction rate is generally slow and a substantial amount of byproducts, such as PACM secondary amines, are formed.

U.S. Pat. Nos. 3,636,108; 3,644,522; 3,697,449 and 4,448,995 teach the base modification of supported ruthenium catalysts with alkali metal and alkaline earth metal salts, including hydroxides, nitrates and sulfates, in the hydrogenation of methylenedianiline to reduce the formation of byproducts.

U.S. Pat. Nos. 3,591,635 and 3,856,862 disclose the use of supported rhodium, as a catalytic metal instead of ruthenium, as a catalyst for MDA hydrogenation to PACM. The rhodium catalyst is base moderated using either ammonium hydroxide as a pretreatment or ammonia in situ. Good hydrogenation rates are achieved with rhodium catalysts in general.

U.S. Pat. No. 4,754,070 describes a catalyst system for the ring hydrogenation of crude methylenedianiline employing ruthenium and rhodium alumina supported catalysts resulting in good hydrogenation rate.

U.S. Pat. No. 5,196,587 discloses a process for the catalytic hydrogenation of crude methylenedianiline using a catalytic pretreatment of the crude methylenedianiline. The process comprises passing the crude feedstock over a ruthenium catalyst carried on an alumina support, cooling, venting hydrogen, filtering, and then hydrogenating the pretreated crude feedstock over a ruthenium/rhodium catalyst.

U.S. Pat. No. 6,184,416 teaches the ring hydrogenation of methylenedianiline using a rhodium catalyst carried on a lithium aluminate support. The inert support allows more effective base modification, which results in better selectivity and higher PACM yield.

U.S. Pat. No. 6,506,361 discloses the use of a monolith reactor in combination with an ejector to effect hydrogenation of organic compounds.

BRIEF SUMMARY OF THE INVENTION

The invention is directed to an improvement in a catalytic process for the ring hydrogenation of a functionalized aromatic compound, viz, a methylenedianiline feedstock, including crude methylenedianiline, i.e., one containing polycyclic oligomers and particularly an improvement in a pretreatment process for such hydrogenation. The improvement in effecting hydrogenation through a pretreatment process resides in passing the crude methylenedianiline feedstock over a ruthenium catalyst carried on a fixed bed support, cooling without venting, and then hydrogenating the pretreated crude methylenedianiline feedstock over a rhodium catalyst or a mixed rhodium/ruthenium catalyst carried on a monolith support and carrying out the ring hydrogenation in a batch reaction.

Significant advantages can be achieved by the practice of the invention, and these include:
- an ability to effect ring hydrogenation of a functionalized aromatic compound in good yield and good reaction rates;
- an ability to operate in an energy efficient manner by avoiding substantial cooling and venting of hydrogen gas and solvent vapor after pretreatment of the crude methylenedianiline feedstock;
- an ability to ring hydrogenate methylenedianiline containing catalyst poisons and polycyclic oligomers thereby extending catalyst life;
- an ability to eliminate difficulties in the handling of hydrogenation catalysts; an ability to use low solvent levels in the hydrogenation process thereby reducing solvent losses;
- an ability to generate hydrogenated methylenedianiline reaction product having a controlled trans, trans isomer content, e.g., from about 20 to 26%; and, an ability to produce a hydrogenated product rich in primary amine functionality.

DETAILED DESCRIPTION OF THE INVENTION

Figure 1:
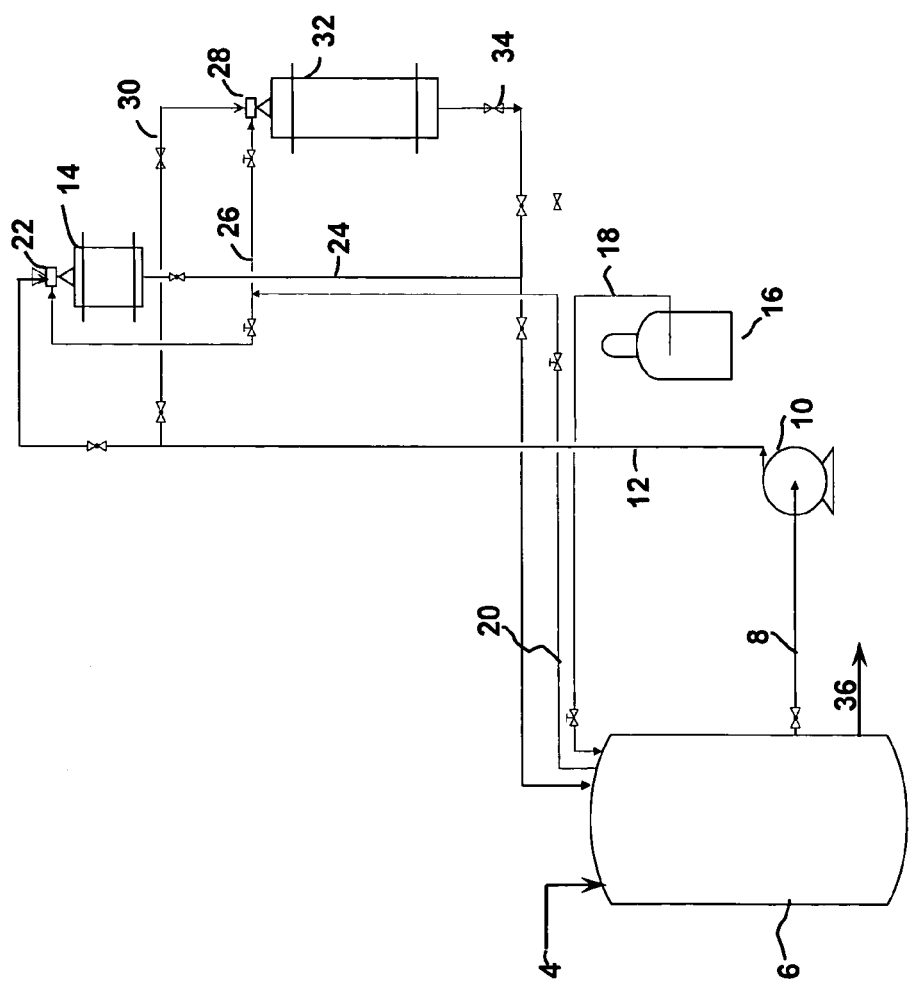
FIG. 1 is a schematic flow diagram describing a process for the hydrogenation of crude methylenedianiline using a fixed bed catalytic pretreatment and catalytic hydrogenation using rhodium or a mixture of rhodium and ruthenium carried on a monolith support.

Methylenedianiline (MDA) is formed by reacting formaldehyde with aniline in the presence of an acid catalyst resulting in a product referred to as MDA-50 and MDA-60. The methylenedianiline formed by the condensation of aniline with formaldehyde includes a large percentage of polycyclic oligomers in the form of 3, 4 and 5 rings. Initially, the 2 ring methylenedianiline product is formed, but as the concentration of methylenedianiline, relative to aniline, increases in the reaction product, the formaldehyde reacts with the thus formed methylenedianiline and oligomers thereof thereby extending the chain. The crude methylenedianiline reaction product often is sold as MDA-85 and MDA-50, i.e., containing 85% and 50%, respectively, of the 2-ring compound.

Surprisingly, it has been found, in a preferred embodiment for the hydrogenation of crude methylenedianiline, that a fixed bed hydrogenation employing pretreatment followed by hydrogenation of the rings affords many advantages. In this embodiment, two catalyst beds are employed, one catalyst based upon the fixed bed pretreatment of the crude methylenedianiline feedstock using ruthenium as the catalyst and the second catalyst bed for the hydrogenation of the pretreated feedstock using a rhodium or a mixture of rhodium and ruthenium carried on a monolith support as the catalyst.

To facilitate an understanding of the pretreatment method for the hydrogenation of crude methylenedianiline, reference is made to the FIG. 1. Crude MDA such as MDA-50, MDA-60, or MDA-85 is charged via line 4 to holding vessel 6. From there, the MDA is conveyed via line 8 to the inlet of pump 10 and from there conveyed via line 12 to pretreatment bed 14. Pretreatment bed 14 consists of a ruthenium catalyst carried on a fixed bed support, such as rings, palls or monolith support as the catalyst system. The ruthenium is present in the pretreatment bed 14 in an amount of about 0.5 to 10%, preferably from 0.5 to 5% by weight of the resulting catalyst. Hydrogen is supplied from tank 16 to the headspace of holding vessel 6 via line 18 and from there via line 20 to jet ejector 22. Jet ejector 22 generates substantial mixing of hydrogen and crude methylenedianiline for introduction and reaction in pretreatment bed 14. The mixture of hydrogen and crude methylenedianiline is supplied at a pressure from about 300 to 2500 psig (2170 to 17,339 kPa), preferably from 750 to 950 psig (5273 to 6652 kPa), at a temperature from 140 to 225° C. Reaction occurs and the reaction product is returned to holding vessel 6 via line 24 and recycle is continued for about one hour or longer as necessary to reduce catalyst poisons.

Once the catalyst poisons have been removed from the crude MDA by the pretreatment process in pretreatment bed 14, the contents in holding vessel 6 are cooled to a temperature of about 100 to 130° C. Cooling is necessary prior to initiating hydrogenation of the pretreated crude methylenedianiline in order to maintain selectivity to the primary amine. The use of the ruthenium catalyst supported in fixed bed mode coupled to holding vessel 6 allows for cooling without venting. In contrast to prior MDA hydrogenation processes involving pretreatment, venting of hydrogen gas and solvent vapor need not be performed, thus eliminating hydrogen and solvent loss not to mention a reducing energy cost of compression.

Hydrogenation of the pretreated crude MDA is effected by opening and closing of appropriate valves in the respective feed lines to jet ejector 28 and hydrogenation zone 32. Hydrogen is conveyed via line 20 and line 26 and pretreated methylenedianiline feedstock in line 30 through jet ejector 28 and then to the hydrogenation zone 32. Hydrogenation is commenced at a temperature typically from about 120 to 130° C. Higher temperatures on initial hydrogenation may result in deamination or loss to secondary amines or both. The reaction product is removed from hydrogenation bed 32 via line 34 and returned to holding vessel 6. Recycling is effected until the desired reaction product is achieved.

In carrying out the hydrogenation, the temperature of the hydrogenation in hydrogenation bed 32 can be increased incrementally to maintain reaction rate once the hydrogenation reaction rate drops by about 20%, as reflected in the hydrogen consumption rate. The rate of hydrogenation of the methylenedianiline drops dramatically when the reaction product is comprised largely of the thus formed half-PACM (half-PACM is used to refer to a reaction product where only one ring is hydrogenated). The ability to increase the temperature in effecting hydrogenation of the second ring of the MDA and the third or higher rings of the oligomers allows one to push the reaction toward complete conversion. A final hydrogenation reaction temperature range in the range from 170 to 225° C. is preferred. Once the desired conversion is obtained, the reaction product can be removed from holding vessel 6 via line 36 and the product purified by conventional methods.

Hydrogenation bed 32 is based upon rhodium, or preferably a mixture of rhodium and ruthenium, carried on a monolith support. The use of a monolith support affords the opportunity to operate over favored conditions. Typically, the rhodium is present in the catalyst system in an amount, based upon its weight as metal, sufficient to provide from 0.1 to 25 weight parts rhodium per 100 weight parts wash coat, preferably 2 to 8 weight parts rhodium per 100 weight parts of wash coat (dry weight). The wash coat is carried on the monolith support in an amount of about 15 to 30%, generally 20% by weight (dry weight) of the monolith support. The catalyst system is formed such that the rhodium to ruthenium weight ratio is from about 1 to 40 parts rhodium per part of ruthenium. Preferably the catalyst system is comprised of from 10 to 25 weight parts rhodium/weight part ruthenium.

The monolith support for the rhodium catalyst is based upon an inorganic porous substrate, a metallic substrate or a carbon based substrate. Examples of substrate components include cordierite, alumina, mullite, etc. Wash coats are based upon alumina with different phases, silica, mixed metal oxides, spinel $LiAl_5O_8$, lithium aluminate, and titanium oxide. Other conventional wash coat support materials can also be used.

Monolith supports are honeycomb structures of long narrow capillary channels, circular, square or rectangular, whereby gas and liquid are co-currently passed through the channels under a laminar flow regime. Typical dimensions for a honeycomb monolith catalytic reactor cell wall spacing range from 1 to 10 mm between the plates. Alternatively, the monolith support may have from 100 to 800, preferably 200 to 600 cells per square inch. Channels or cells may be square, hexagonal, circular, elliptical, etc. in shape.

With these catalyst systems, one can effectively hydrogenate methylenedianiline feedstocks in good yield and excellent reaction rates having approximately 55 to 90% of the 2 ring product and upwards of 50%, typically 20% oligomer, i.e., three or more ring methylene bridged polyphenylamine formamides (MDA-85) using a rhodium/ruthenium catalyst carried on a monolith. Even excellent hydrogenation of these feeds, which contain byproducts which are poisons to rhodium catalysts, also can be achieved.

Alkali moderation, i.e., base modification or in situ base moderation is a preferred mode of operation and is important in achieving high selectivity to primary amine. A limited amount of $NH_3$, LiOH, NaOH, KOH, and $Li_2CO_3$ as base modifiers, 0.1 to 15% (preferred at 0.5% or below based upon catalyst metals) can be used to pretreat the catalyst and effect what may be referred to as alkali moderation.

As with conventional processes, the hydrogenation of methylenedianiline is carried out under liquid phase conditions. Liquid phase conditions are maintained typically by carrying out the hydrogenation in the presence of a solvent. Although as reported in the art, it is possible to effect reaction in the absence of a solvent, the processing usually is much simpler when a solvent is employed. Representative solvents suited for effecting hydrogenation of aromatic amines include saturated aliphatic and alicyclic hydrocarbons such as cyclohexane, hexane, and cyclooctane; low molecular weight alcohols, such as methanol, ethanol, isopropanol; and aliphatic and alicyclic hydrocarbon ethers, such as n-propyl ether, isopropyl ether, n-butyl ether, amyl ether, tetrahydrofuran, dioxane, and dicyclohexylether. Tetrahydrofuran is the preferred solvent.

When a solvent is used, it can be used in concentrations as low as 20% by weight based upon the methylenedianiline introduced into the hydrogenation zone and typically the solvent is used at levels from about 25 to 150% by weight of the crude methylenedianiline. Higher levels of solvent may be used but offer no significant advantages.

The following examples are intended to illustrate various embodiments of the invention and all parts and percentages given are weight parts or weight percents unless otherwise specified.

General Procedure/Non Pretreatment

The following catalysts are used in the experiments:
1. Rhodium/ruthenium bimetallic with alumina wash coat: rhodium/ruthenium 4/1 (w/w), total metal loading: 225 g metal/cu. ft, on alumina wash coat and a cordierite monolith substrate.
2. Ruthenium with lithium aluminate wash coat for MDA pretreatment: metal loading: 80 g/cu. ft with a cordierite monolith substrate.
3. Rhodium/ruthenium bimetallic with lithium aluminate wash coat: rhodium/ruthenium 8/1, total metal loading: 198 g metal/cu. ft, on lithium aluminate wash coat and a cordierite monolith substrate.
4. Slurry catalysts for comparison: 16.25 g of 4% rhodium on alumina and 3.2 g ruthenium on alumina (as equivalents to the rhodium and ruthenium monolith of a 2 inches long and 2 inches in diameter block used: 0.65 g rhodium and 0.16 g ruthenium).

The feed material employed is a crude methylenedianiline (MDA). A typical sample of the crude MDA used in this process contains 88%, MDA, 10% three ring methylene bridged polyphenylamines, 1% four ring methylene bridged polyphenylamines (and higher), and less than 1% (including 0.2% MDA-formamide and smaller amounts of three or more ring methylene bridged polyphenylamine formamides). The feed is referred to as MDA-85.

All reactions were carried out in a 2 liter high pressure stainless steel reactor modified to have a stainless steel basket to hold a piece of monolith catalyst (2 inches long and 2 inches in diameter) directly underneath the agitator. The current generated by agitation during reaction causes the reaction medium to pass through the channels of the monolith catalyst, either downwardly or upwardly depending on the internal flow generated by the agitation system. Such modification of a stirred tank reactor allows for testing of a monolith fixed bed catalyst in a stirred batch reactor.

The monolith catalyst is first reduced in hydrogen. The reactor with the monolith catalyst is leak checked with i-PrOH under 55 bar $N_2$. It is then purged with $N_2$ (25 bar, 3 times) and with $H_2$ (25 bar, 3 times). During each purge step, the agitator is turned on for 1 min, then turned off before degassing. Finally, the reactor is charged with 55 bar $H_2$ and heated to 180 to 190° C. with stirring for 4 hours.

EXAMPLE 1

Two-Step Hydrogenation of Methylenedianiline (MDA) to Bis (Para-Aminocyclohexylmethane) (PACM)

The purpose of this example is to determine whether a ruthenium pretreatment using a ruthenium coated monolith catalyst would be effective to destroy catalyst poisons and then effective to permit ring hydrogenation using a rhodium impregnated monolith catalyst.

A two-step reaction in which the MDA feed was first pretreated over a 5% ruthenium monolith catalyst having a lithium aluminate wash coat at 20% add-on and then hydrogenated over rhodium and ruthenium bi-metallic monolith catalyst weight ratio of rhodium to ruthenium 8:1 treated with a lithium aluminate wash coat per the flow scheme described in FIG. 1. Hydrogenation was continued until the consumption of hydrogen required to hydrogenate 5–10% of the crude methylenedianiline feedstock. Then, the pretreated methylenedianiline was fully hydrogenated to convert the remaining 95% of the crude reaction product. The results are shown in Table 1.

The use number in Table 1 gives the consecutive hydrogenation reaction test with the same catalyst. The T95 refers to time, in minutes, required to achieve 95% conversion of the MDA feed, which is based on the hydrogen consumed by the reaction for complete conversion. The PACM secondary amines refer to the by-product formed during the reaction, and both PACM and PACM secondary amines are expressed in weight percent of the product. The last column in Table 1 gives the MDA and tetrahydrofuran (THF) concentration (weight %) in the feed mix.

TABLE 1

Hydrogenation Of Pretreated MDA Using Rhodium/Ruthenium Monolith Catalyst With Lithium Aluminate Wash coat

| Use | T95 (min) | PACM (%) | PACM secondary amines (%) | MDA/THF (w/w) |
|-----|-----------|----------|---------------------------|---------------|
| 1 | 55 | 86.5 | 1.8 | 50/50 |
| 2 | 47 | 85.0 | 1.7 | 50/50 |
| 3 | 44 | 85.0 | 1.2 | 50/50 |
| 4 | 65 | 84.9 | 1.4 | 50/50 |
| 5 | 59 | 83.7 | 2.1 | 50/50 |
| 6 | 57 | 85.3 | 1.7 | 50/50 |
| 7 | 58 | 82.5 | 2.6 | 65/35 |
| 8 | 60 | 84.4 | 1.6 | 50/50 |
| 9 | 60 | 81.6 | 2.6 | 65/35 |

As shown in Table 1, the MDA feed used was first pretreated with ruthenium monolith catalyst. The pretreatment at the 5% level apparently was sufficient to reduce the level of rhodium catalyst poisons in the commercial MDA feed to a negligible level.

Reduction of catalyst poisons was believed to be the major contributor toward favorable ring hydrogenation since the rhodium/ruthenium monolith catalyst employed for ring hydrogenation offered consistent results in terms of rate and catalyst life. Reaction times varied only in a narrower range.

The data show that going from 50 to 65% MDA in the feed (less solvent) did not show an adverse effect. Hydrogenation to PACM remained consistent as did low secondary amine formation (<3%).

EXAMPLE 2

Hydrogenation of MDA to PACM Employing Rh/Ru Alumina Coated Monolith Catalyst

The feasibility of hydrogenating crude MDA to PACM employing a monolith catalyst was demonstrated using a one-step reaction employing a rhodium and ruthenium bi-metallic carried on a monolith substrate with an alumina wash coat. In contrast to the hydrogenation bed in the two-step pretreatment process, Example 1, a higher level of ruthenium is required. The rhodium to ruthenium ration is from 4 to 15 weight parts rhodium per weight part ruthenium. The result of this reaction was then compared to slurry catalyst under same metal loading and reaction conditions.

The hydrogenation of MDA is carried out by charging the reactor with 1000 g of MDA/THF (50/50 or 65/35) solution. The reaction mixture is then brought to 180° C., 55 bar hydrogen with stirring. The progress of the reactor is monitored by the rate of hydrogen uptake. The reaction is complete when the rate of hydrogen uptake is less than 1 liter/min. Once the product is cooled to room temperature, it is drained through a valve at the bottom of the reactor. A fresh charge of MDA/THF is added and the catalyst undergoes multiple uses.

In the first 2 runs, there was no alkali moderation of the MDA hydrogenation. In uses 3 and 4, alkali moderation was done by adding LiOH to the reaction mixture and thus moderating the hydrogenation reaction in situ. In the next series of runs, i.e., uses 5–11, the monolith catalyst, after deposition of rhodium and ruthenium on the monolith support, was treated with LiOH to provide for base modification of the catalyst. Before use 5, then, LiOH (7 g) as 10% aqueous solution was added to 1000 g of isopropanol. The monolith catalyst was submerged in the mixture with stirring at 190° C., 800 psig hydrogen for 16 hours.

Table 2 lists the results from MDA hydrogenation using a monolith catalyst with alumina wash coat. For comparison, MDA hydrogenation using slurry catalyst, (4%) Rh/gamma alumina and (5%) ruthenium/gamma alumina, with same metal to MDA loading as in monolith case, was carried out under the same conditions as described above. The results are listed in Table 3.

TABLE 2

MDA Hydrogenation Using Rhodium/Ruthenium Monolith Catalyst With Alumina Wash coat

| Use | T95 (min) | PACM (%) | PACM secondary amines (%) |
| --- | --- | --- | --- |
| 1 | 52 | 62.1 | 19.3 |
| 2 | 52 | 60.4 | 16.0 |
| 3 | 64 | 57.1 | 22.5 |
| 4 | 64 | 63.8 | 19.0 |
| 5 | 85 | 71.8 | 5.5 |
| 6 | 93 | 73.1 | 4.6 |
| 7 | 95 | 71.5 | 4.2 |
| 8 | 102 | 72.3 | 4.1 |
| 9 | 103 | 74.7 | 6.1 |
| 10 | 93 | 75.4 | 6.2 |
| 11 | 89 | 77.6 | 4.6 |

TABLE 3

MDA Hydrogenation Using Rhodium/Ruthenium Slurry Catalysts

| Use | T95 (min) | PACM (%) | PACM secondary amines (%) |
| --- | --- | --- | --- |
| 1 | 56 | 73.5 | 9.7 |
| 2 | 55 | 72.6 | 10.2 |
| 3 | 51 | 67.4 | 15.3 |
| 4 | 44 | 79.4 | 3.2 |

The results in Table 3 show that conventional MDA hydrogenation effected in the presence of rhodium/ruthenium slurry catalyst system produces PACM and its related coupled byproducts, and PACM secondary amines.

Use 4 of the slurry catalyst, as shown in the Table 3, demonstrates the effect of in situ LiOH addition to the reaction medium. In the $4^{th}$ use, LiOH (0.9 g) as 10% aqueous solution was added with the MDA feed, and as the data shows, the addition of the base effectively suppressed the formation of PACM secondary amines. The secondary amine level decreased from 15.3% to 3.2%.

In summary, a rhodium/ruthenium catalyst carried on a monolith support, preferably one using lithium aluminate as a wash coat, results in high selectivity to PACM (Table 1). With an lithium aluminate wash coat, LiOH base modification was effective when done during the pre-reduction of the catalyst or in situ, and further, the effect was long lasting. PACM secondary amines were kept low (<3%) in all uses. Changing feed concentration from 50% in THF to 65% did not impact reaction rate.

The use of the two step process as described in Example 1 allows for effective hydrogenation without requiring venting of hydrogen gas and solvent vapor and substantial cooling of the reaction product, e.g., cooling to a temperature of below 100° C.

The invention claimed is:

1. In a process for the ring hydrogenation of crude methylenedianiline, wherein said methylenedianiline is contacted with hydrogen in the presence of a catalyst, the improvement which comprises:
    pretreating the crude methylenedianiline feedstock by partially hydrogenating said feedstock in the presence of a catalyst comprised of ruthenium carried on a fixed bed support to produce a pretreated feedstock; and then,
    hydrogenating the pretreated feedstock in the presence of a catalyst comprised of rhodium carried on a monolith support incorporating a wash coat.

2. The process of claim 1 wherein the catalyst comprised of rhodium carried on a monolith support also includes ruthenium in an amount from 1 to 40 weight parts rhodium per weight part ruthenium.

3. The process of claim 2 wherein the combination of rhodium and ruthenium is carried on said monolith support in an amount of from 0.5 to 5% by weight of the wash coat and the weight parts rhodium per weight part ruthenium is from 10 to 25.

4. The process of claim 3 wherein the wash coat is comprised of a support material selected from the group consisting of alumina, silica, mixed metal oxides, spinel $LiAl_5O_8$, lithium aluminate, and titanium oxide.

5. The process of claim 4 wherein the ruthenium is carried on a monolith support.

6. The process of claim 5 where the pretreatment of said crude methylenedianiline feedstock is carried out at a temperature of 140 to 225° C.

7. The process of claim 6 wherein the pretreated feedstock from the pretreatment is cooled to a temperature of from 100 to 130° C. without venting of hydrogen gas and solvent vapor prior to conducting hydrogenation of said pretreated feedstock.

8. The process of claim 7 wherein the temperature for hydrogenation of the pretreated feedstock is increased incrementally from 100 to 130° C. to a final temperature of from 170 to 225° C.

9. The process of claim 8 wherein the pretreatment pressure is from 300 to 2500 psig.

10. The process of claim 9 wherein the Rh/Ru catalyst is treated with base modifier to limit secondary amine formation, the base modifier selected from the group consisting of ammonia, lithium hydroxide, sodium hydroxide, potassium hydroxide, and lithium carbonate.

11. In a process for the ring hydrogenation of crude methylenedianiline wherein said methylenedianiline is contacted with hydrogen in the presence of a catalyst, the improvement which comprises:

employing a catalyst comprised of rhodium and ruthenium carried on a monolith support.

12. The process of claim 11 wherein the monolith support incorporates a wash coat for the monolith support and said wash coat is comprised of a support material selected from the group consisting of alumina, silica, mixed metal oxides, spinel $LiAl_5O_8$, lithium aluminate, and titanium oxide.

13. The process of claim 12 wherein the rhodium is provided in an amount, based upon its weight as metal, sufficient to provide from 0.1 to 25 weight parts rhodium per 100 weight parts wash coat (dry weight).

14. The process of claim 13 wherein a catalyst system is formed such that rhodium and ruthenium are present and the rhodium to ruthenium weight ratio is from about 4 to 15 weight parts rhodium per weight part of ruthenium.

15. The process of claim 14 wherein the catalyst is treated with a base modifier selected from the group consisting of ammonia, sodium hydroxide, potassium hydroxide, lithium hydroxide, and lithium carbonate.

16. The process of claim 15 wherein the monolith support has from 100 to 800 cells per square inch.

17. The process of claim 16 wherein the reaction is carried out at a temperature of from 130 to 225° C.

18. The process of claim 17 wherein the reaction pressure is from 700 to 2500 psig.

19. The process of claim 18 wherein the crude methylenedianiline feedstock is MDA-85.

* * * * *